(12) United States Patent
Huynh (10) Patent No.: US 9,795,703 B2
(45) Date of Patent: Oct. 24, 2017

(54) DEVICE FOR DIFFUSING A COMPOUND

(71) Applicant: DC & BV France Holding SAS, Paris (FR)

(72) Inventor: Valery Huynh, Chelles (FR)

(73) Assignee: DC & BV France Holding SAS (FR)

( * ) Notice: Subject to any disclaimer, the term of this patent is extended or adjusted under 35 U.S.C. 154(b) by 39 days.

(21) Appl. No.: 14/894,915

(22) PCT Filed: Aug. 1, 2014

(86) PCT No.: PCT/EP2014/066618
§ 371 (c)(1),
(2) Date: Nov. 30, 2015

(87) PCT Pub. No.: WO2015/106842
PCT Pub. Date: Jul. 23, 2015

(65) Prior Publication Data
US 2016/0101206 A1    Apr. 14, 2016

(30) Foreign Application Priority Data
Jan. 15, 2014   (EP) ..................................... 14151229

(51) Int. Cl.
*A61L 9/12* (2006.01)
*B05B 3/10* (2006.01)
*B05B 7/00* (2006.01)
*A01M 1/20* (2006.01)

(52) U.S. Cl.
CPC ............ *A61L 9/12* (2013.01); *A01M 1/2033* (2013.01); *B05B 3/10* (2013.01); *B05B 7/0012* (2013.01); *A61L 2209/134* (2013.01)

(58) Field of Classification Search
CPC ..... A61L 9/00; A61L 9/04; A61L 9/12; A61L 9/122
USPC .......................................................... 422/124
See application file for complete search history.

(56) References Cited

U.S. PATENT DOCUMENTS

| 5,370,829 | A  | * | 12/1994 | Kunze  | ..................... | A61L 9/122 261/24 |
| 2007/0248461 | A1 | * | 10/2007 | Lee    | ......................... | F04D 17/06 415/220 |
| 2013/0328223 | A1 | * | 12/2013 | Sharma | ............... | A01M 1/2033 261/104 |

FOREIGN PATENT DOCUMENTS

WO    2013133428 A1    9/2013

OTHER PUBLICATIONS

International Search Report and Written Opinion for Application No. PCT/EP2014/066618 dated Nov. 11, 2014.

\* cited by examiner

*Primary Examiner* — Sean E Conley
(74) *Attorney, Agent, or Firm* — Lerner, David, Littenberg, Krumholz & Mentlik, LLP (57) ABSTRACT

The present invention provides a device for diffusing a compound comprising: a chamber arranged to store a compound, wherein the chamber includes an agitator member arranged to disturb the compound within the chamber to diffuse the compound into air within the chamber.

12 Claims, 7 Drawing Sheets

PERSPECTIVE VIEW (FRONT)    PERSPECTIVE VIEW (REAR)

DEVICE FOR DIFFUSING A COMPOUND

CROSS-REFERENCE TO RELATED APPLICATIONS

The present application is a national phase entry under 35 U.S.C. §371 of International Application No. PCT/EP2014/066618 filed Aug. 1, 2014 published in English, which claims priority from EP Application No. 14151229.3 filed Jan. 15, 2014, all of which are incorporated herein by reference.

TECHNICAL FIELD

The present invention relates to a device for diffusing a compound and particularly, although not exclusively, to a device for diffusing a chemical compound such as a scented chemical substance.

BACKGROUND

Many people enjoy being in the presence of an environment whereby the surrounding air has been scented or freshened. To increase the pleasantness of an environment, various products, such as air fresheners or scented oil diffusers have been placed on the market for users to alter the scent of a particular space.

However, despite the various products which are available, none of these air fresheners are able to properly diffuse a scented compound in a uniform manner that would allow a space to be maintained in a freshen state. Typical problems which are encountered by users of air fresheners is that once an air-freshener is realised for operation, the duration of its effectiveness cannot be controlled. On the other hand, more sophisticated units such as electronic controlled air-fresheners which dispense scented compounds at predetermined intervals are able to control the usage of the scented compounds, but are not able to respond to individual events that require more scented compounds to be diffused, thus resulting in a poor application of the scented chemical to the surrounding environment.

SUMMARY OF THE INVENTION

In accordance with a first aspect of the present invention, there is provided a device for diffusing a compound comprising:

a chamber arranged to store a compound, wherein the chamber includes an agitator member arranged to disturb the compound within the chamber to diffuse the compound into air within the chamber.

In an embodiment of the first aspect, the agitator member is arranged to disturb the compound such that air outside of the chamber is at least partially drawn into the chamber.

3. A device for diffusing a compound in accordance with In an embodiment of the first aspect, the agitator member is further arranged to disturb the compound such that the air within the chamber is at least partially released from the chamber.

In an embodiment of the first aspect, the agitator member includes at least one conduit arranged to provide liquid communication between a base portion of the chamber and a top portion of the chamber.

In an embodiment of the first aspect, the agitator member disturbs the compound within the chamber, the compound is arranged to flow from the base portion of the chamber to the top portion of the chamber.

In an embodiment of the first aspect, the agitator member is arranged to rotate so as to apply centrifugal force onto the compound within the chamber.

In an embodiment of the first aspect, the centrifugal force is arranged to drive the compound from the base portion of the chamber to the top portion of the chamber.

In an embodiment of the first aspect, the compound reaches the top portion of the chamber, the compound is propelled from the agitator member towards a sidewall of the chamber.

In an embodiment of the first aspect, the compound is diffused into the air within the chamber when the compound is propelled from the agitator member.

In an embodiment of the first aspect, the agitator member is of a truncated horn shape or frustum shape.

In an embodiment of the first aspect, the agitator member is rotated by a shaft connected to a motor.

In an embodiment of the first aspect, the motor is housed in a support base below the chamber.

In an embodiment of the first aspect, the compound includes a scented chemical substance.

In accordance with a second aspect of the present invention, there is provided a device for distributing a chemical compound to surrounding air comprising:

a chamber arranged to diffuse the chemical compound to the air within the chamber, wherein the chamber includes a cycling mechanism arranged to draw and diffuse the chemical compound within the air of the chamber; and a vent arranged to permit air to enter and exit the chamber.

In an embodiment of the second aspect, the cycling mechanism is further arranged to draw the chemical compound from a base of the chamber to the top of the chamber.

BRIEF DESCRIPTION OF THE DRAWINGS

Embodiments of the present invention will now be described, by way of example, with reference to the accompanying drawings in which.

DETAILED DESCRIPTION OF THE PREFERRED EMBODIMENT

Figure 1:
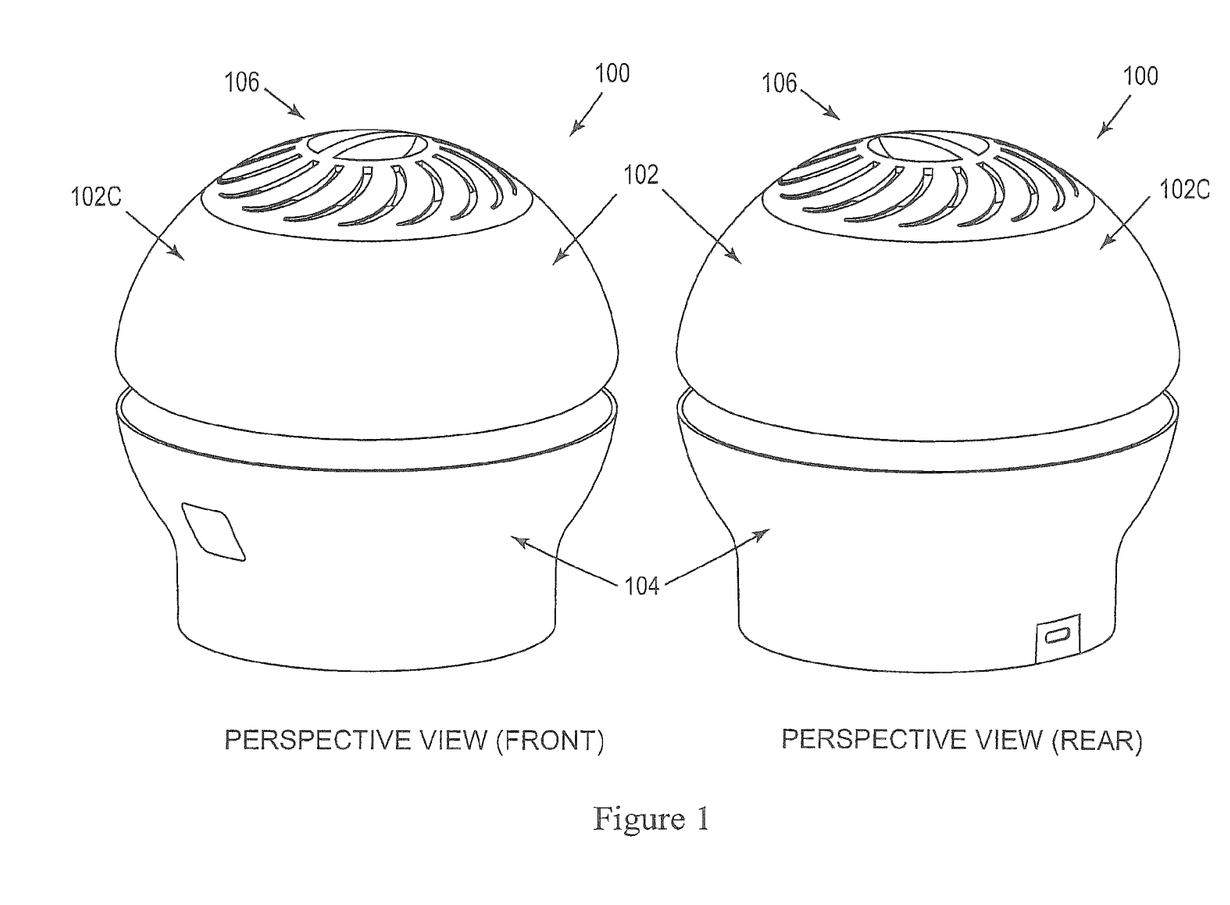
FIG. 1 is a front and rear perspective view of a device for diffusing a compound in accordance with one embodiment of the present invention.
Figure 2:
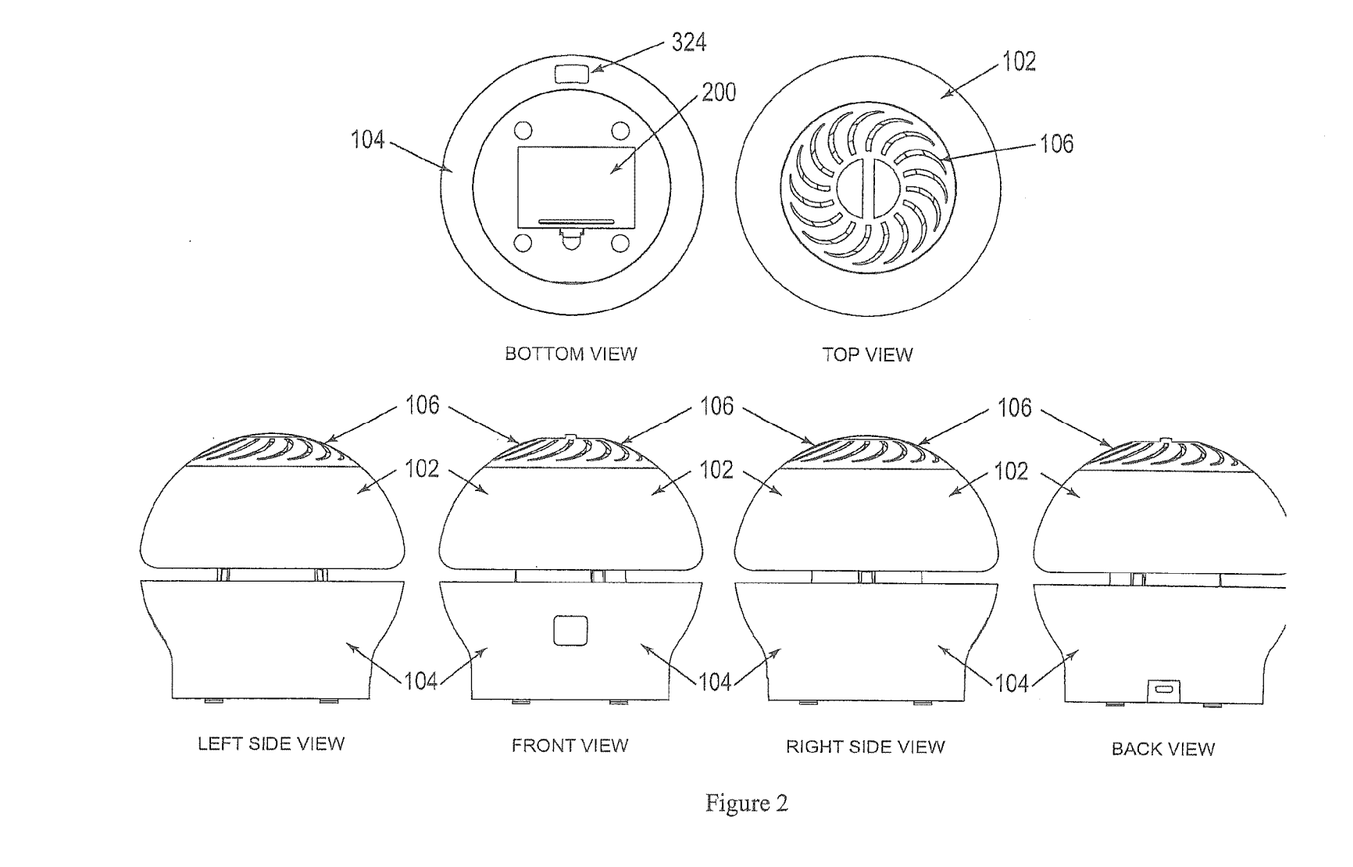
FIG. 2 is a top, bottom, left side, right side, front and rear view of the device of FIG. 1.
Figure 3:
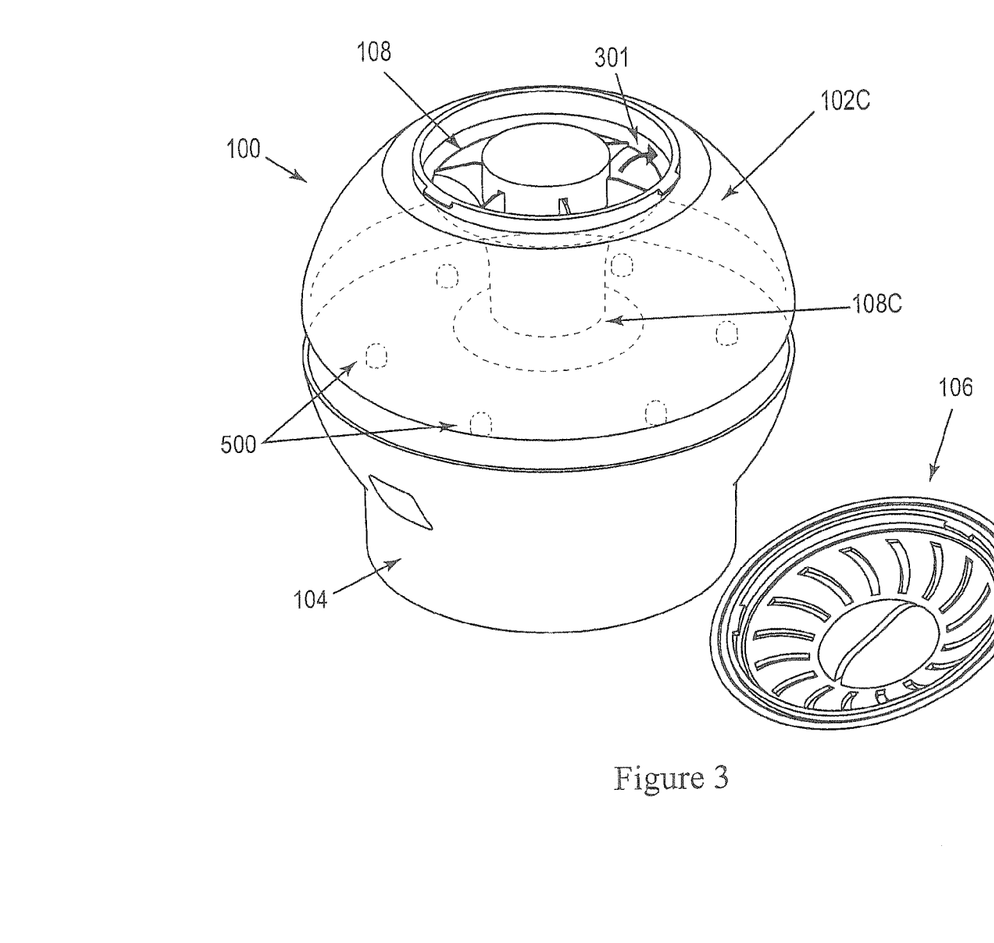
FIG. 3 is an illustration of the device of FIG. 1 with the diffuser cover removed.

Referring to FIGS. 1, 2 and 3, there is illustrated an embodiment of a device for diffusing a compound 100 comprising: a chamber arranged to store a compound, wherein the chamber includes an agitator member arranged to disturb the compound within the chamber to diffuse the compound into air within the chamber.

In this embodiment, the device 100 includes a chamber 102C which is arranged to provide a space in which a chemical compound can be diffused into the air within the chamber 102C and in turn, arrange for the air within the chamber to be released into the exterior of the chamber whilst arranging for air from outside of the chamber to be drawn into the chamber 102C so as to allow the chemical compound to be diffused to the air drawn in. As shown, the chamber is partially defined by a compound container 102 disposed on a support base 104 of the device 100. The compound container 102, which may be a container or tank 102 made from a transparent material as shown in FIG. 3 or a non-transparent material as shown in FIGS. 1 and 2 is arranged to be partially filled with a chemical compound which is intended to be diffused by the device 100 into the surrounding atmosphere during operation of the device 100.

Preferably, the chemical compound may be a mixture of an aromatherapy or scent substances and a diluting agent such as water. In some examples, the chemical compound may also be alcohol or disinfectant based in which case the device may also provide a disinfectant function. It is important to appreciate that the chemical compounds diffused need not be liquid, but can be a fluid of various viscosity or a collection of fine particles, larger solid particles or a combination of one or more of these chemicals of having one or more of these properties. As an example, micro carbon particles may be added to a mixture of an aromatherapy substances and water to provide carbon absorption of pollutants.

In this embodiment, the device 100 includes an agitator member 108, which is hidden from view in FIGS. 1 and 2 but more clearly shown in FIG. 3. The agitator member 108 is arranged to be disposed within the chamber 102C. As shown in these examples, the agitator member 102 is of a truncated horn or truncated cone shaped and is arranged to rotate about an axis on or near the centre of the chamber 102C. Preferably, the agitator member 108 is arranged to have a narrow end towards the base portion of the container 102 or chamber 102C whilst its wider end is disposed towards the upper or top portion of the chamber 102C.

As shown, the agitator member 108 provides a conduit 108C or channel which provides liquid communication between the base portion of the chamber 102C and the top portion of the chamber 1020. In this regard, once the chamber 102C is partially filled with a liquid, such as the chemical compound being diffused by the device 100, and the agitator member 108 is rotated about its axis, portions of the chemical compounds in contact with the narrow end of the agitator member 108 is then drawn up by centrifugal force towards the upper end of the agitator member 108 towards the top of the chamber 102C via the conduit 1080, which in this example is defined by the inner surfaces of the agitator member 108 and a rotational axis arranged to drive the rotation of the agitator member 108.

By rotating the agitator member 108 as shown, the chemical compounds stored within the chamber 102C are then drawn upwards towards the top end of the chamber 102C by centrifugal force. Once the chemical compounds are drawn to the top of the agitator member 108, the agitator member 108 may then propel the chemical compounds towards the side walls of the chamber 102C. Preferably, the agitator member 108 has a flat profile, like those of the end of a horn, towards the top of the chamber 102C whereby when the chemical compounds drawn upwards by the agitator member 108 is flung by the spinning agitator member towards the side walls of the chamber 102C, and in this process, forms a spray or mist of the chemical compounds adjacent to the top end of the chamber 102C towards the chamber's side wall. This in turn allows a substantial portion of the air within the chamber 102C to mix with the spray or mist of the chemical compound propelled by the agitator member 108 and thus allowing for the chemical compound to be diffused into the air within the chamber 102C.

As the agitator member 108 is arranged to rotate about its axis whilst drawing the chemical compounds from the base of the chamber 102C to the top of the chamber 102C where it will fall to the base of the chamber for a continuous cycling of this process, the agitator member 108 in turns disturbs the chemical compounds within the chamber 102C. Through this continuous disturbance, a suction draft may be formed within the chamber 102C from the rotation of the agitator member 108 and the rotational flow of the chemical compounds within the chamber 102C to draw air from outside of the chamber 102C to within the chamber and in turn, expel this air out of the chamber again.

During this continuous cycle of diffusing the chemical compound, the air in the chamber 102C is continually mixed with the droplets or spray of the chemical compounds being propelled by the rotating agitator member 108. Accordingly, the process allows for the chemical compound to be diffused into the air around the device 100.

Figure 4A:
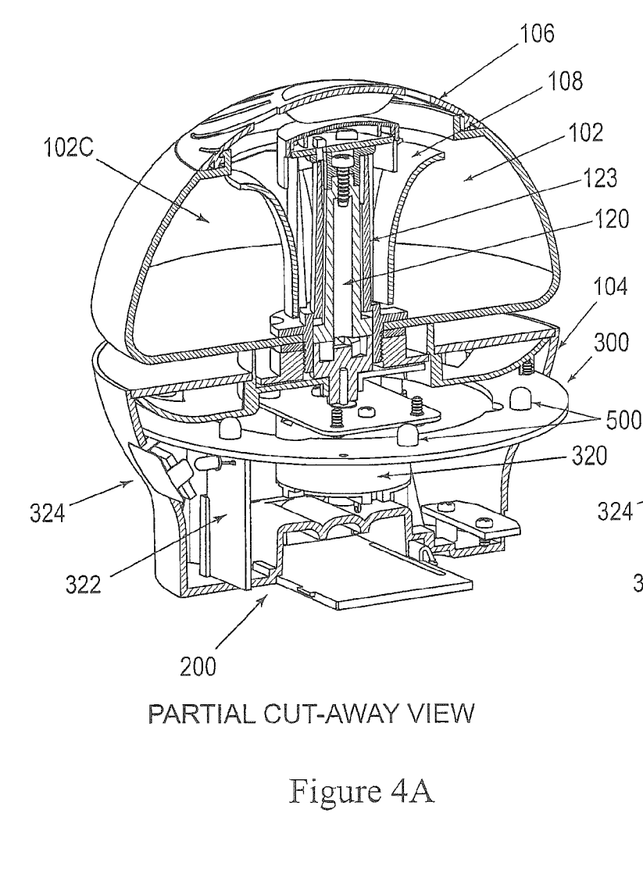
FIG. 4A is a cut away view of the device of FIG. 1.
Figure 4B:
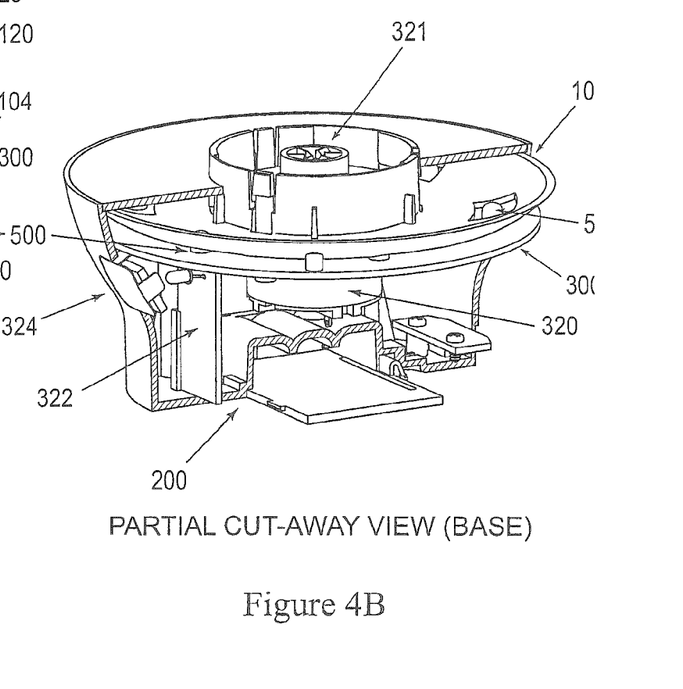
FIG. 4B is a cut away view of a support base of the device of FIG. 1.

With reference to FIGS. 4A and 4B, there is illustrated a cut away view of the device for diffusing a compound 100. In this embodiment, the compound container generally defines the chamber 102C which permits the mixing of the chemical compounds with the air within the chamber 102C. The chamber 102C has an opening towards the top of the container 102 wherein a vent, formed as part of the diffuser cover 106 encloses the chamber 102 itself. The diffuser cover 106, which is optional, allows air to be drawn into the chamber 102C whilst allowing the air to be expelled from the chamber 102C. Preferably, the vents disposed on the diffuser cover 106 is defined from a plurality of spirally slots which in turn fits the profile of the suction of air and expulsion of air to and from the chamber caused by the rotating agitating member 108 within the chamber 102C.

Figure 5A:
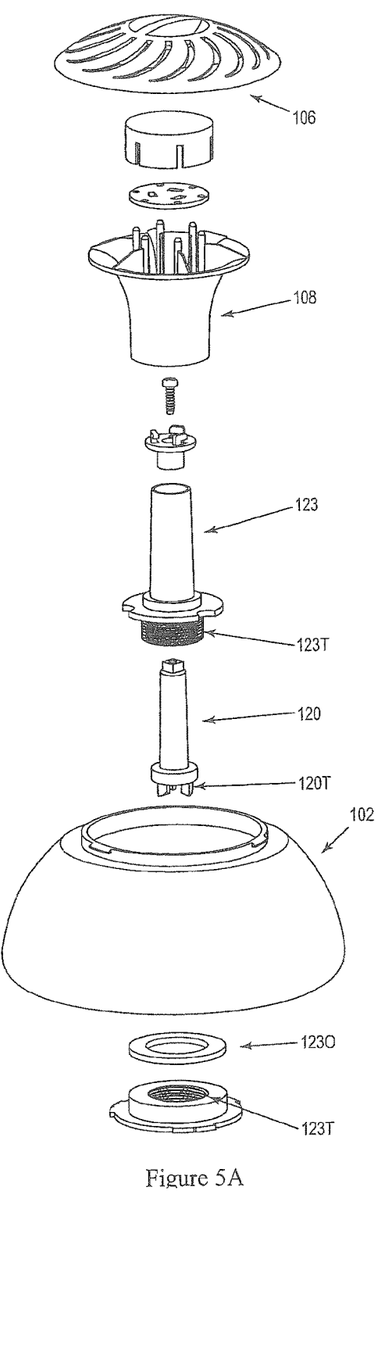
FIG. 5A is an exploded view of a compound container of the device of FIG. 1.
Figure 6:
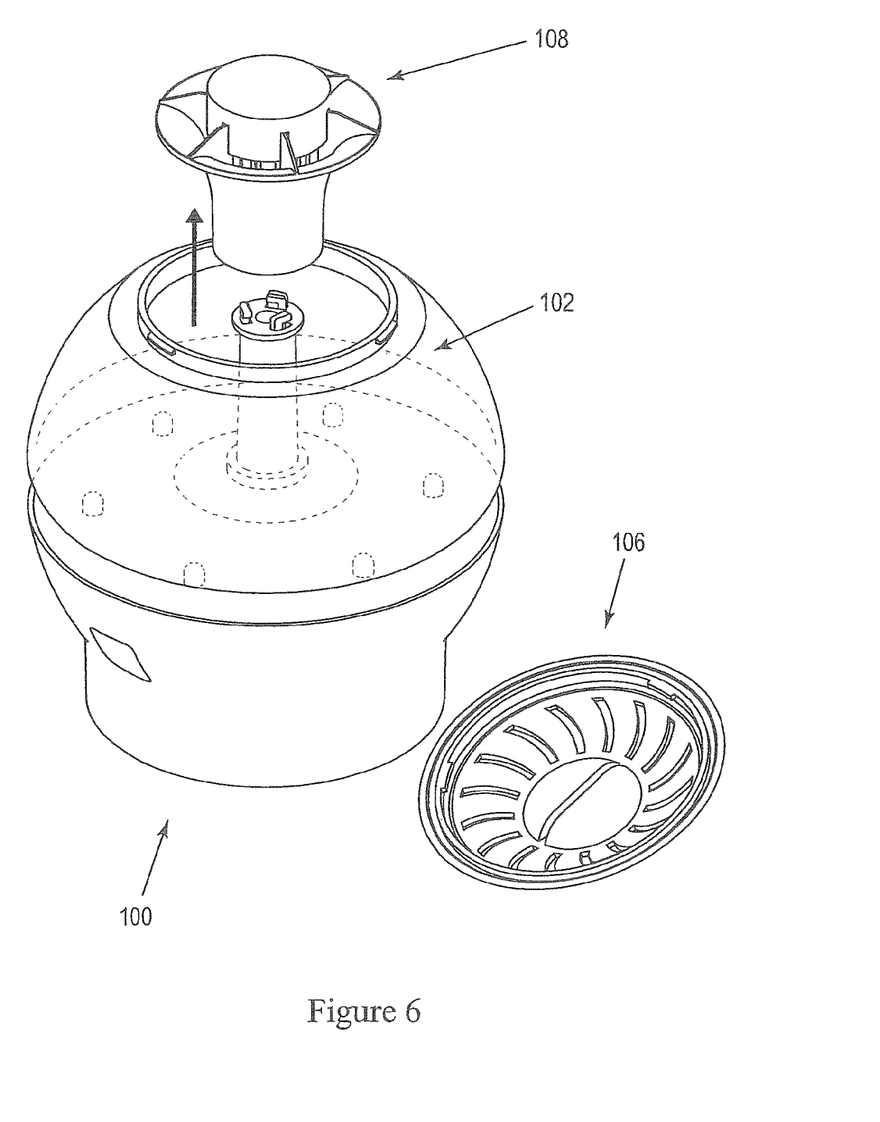
FIG. 6 is an illustration of the device of FIG. 1 with an agitator member being removed.
Figure 7:
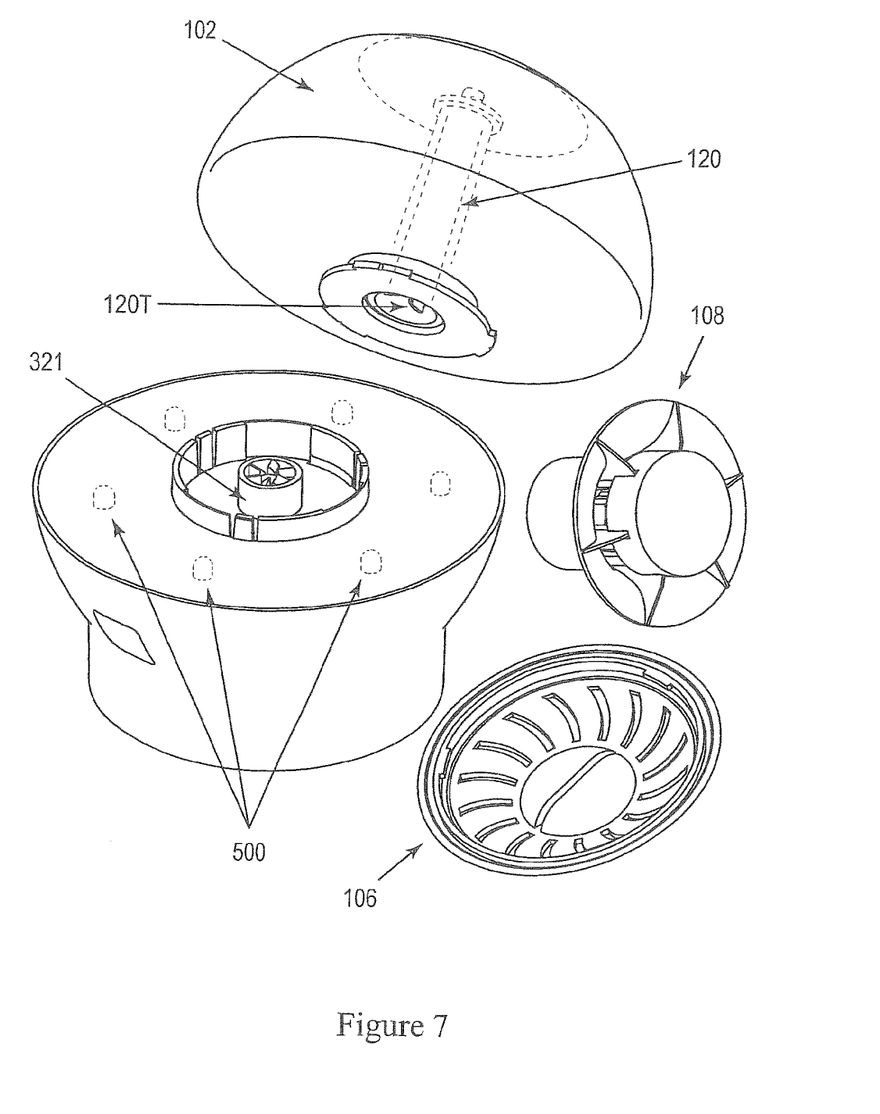
FIG. 7 is an illustration of the device of FIG. 1 with an agitator member and a compound container being removed.

In this example embodiment, the agitating member 108 is driven by a shaft 120 which is arranged to extend into the support base 104 of the device 100 where an electric motor 320 is arranged to drive the shaft 120 so as to rotate the agitating member 108. As illustrated in FIGS. 4A and 5A, the shaft 120 may have a liquid proof cover 123 which is arranged to cover and substantially surround the shaft 120 such that the chemical compounds stored within the chamber 102C will not leak into the shaft 120 or motor 320 in the support base 104. Preferably, a series of threads 123T and rings 1230 disposed on the cover 123 or other fasteners are arranged to be tightened together to form a water tight seal around the shaft 120. Alternatively, as shown in FIGS. 6 and 7, in an alternative embodiment, the cover 123 for the shaft 120 is formed as part of an integrated hollow structure within the container 102 and allows a shaft 120 to be placed within the hollow structure moulded within the container 102 itself. This is advantageous in that the inner walls of the chamber will ensure no release of liquid from the container 102 and into the shaft 120 or motor 320 is possible.

Figure 5B:
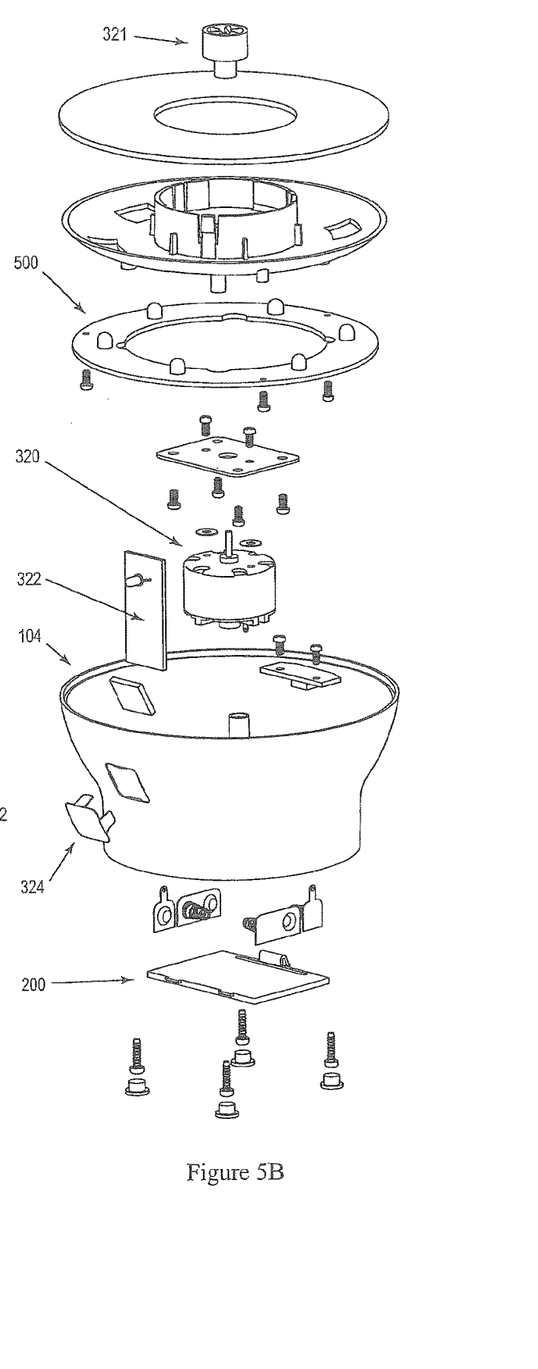
FIG. 5B is an exploded view of a support base of the device of FIG. 1.

In the embodiment of the device as shown in FIGS. 4A, 4B and 5B, the support base 104 of the device 100 has an electric motor 320 arranged to power the agitator member 108. The electric motor 320 is in connection with a transmission gear member 321 which in turn is arranged to interact with the teeth 120T of the shaft 120 so as to drive the shaft 120 when the motor 320 is actuated. A power source, in the form of a battery housing 200 arranged to receive one or more batteries is also provided below the motor 320 so as to supply electrical power to the motor 320, although as a person skilled in the art would appreciate, an external power source such as a mains power may also be used to power the electric motor 320. The electric motor 320 may also be controlled by an actuator 324 which allows touch or switch operation of the device 100 and actuation of the motor 320. Electronic control circuits may also be added to a Printed Circuit Board (PCB) 322 to control the speed of the electric motor 320, and thus the rotational speed of the agitating member 108 to diffuse more or less of the chemical compound.

Preferably, as shown in this embodiment, numerous light emitting diodes (LEDs) 500 are disposed in an annular fashion around the support base of the device 100. These LEDs 500 provide lighting to the device 100 and particularly in embodiments where the container 102 is made from a substantially transparent material, the presences of the LEDs 500 adds to the effect and aesthetic appeal of the device 100 overall. In some advanced embodiments, Ultra Violet LEDs may be used to disinfect the chemical compounds within the chamber 102C itself.

With reference to FIGS. 6 and 7, another embodiment of the device is shown. In this embodiment, the device 100 for diffusing a compound includes a number of components which are all modular such that they can be removable engaged with each other by using a tooth and slot fit. In this example, the container 102, agitator member 108 and shaft 120 are all modular in that they fit together by use of a locking system comprising of locking teeth and slots arranged to fit together to lock the components together to form the device 100. This is advantageous in that disassembly and reassembly of the device is fast and easy and thus making the cleaning process of the device highly efficient.

In one example of operation, a user may firstly open the diffuser cover 106 exposing the container 102 and the agitator member 108 for access. Once access is available, the user may firstly pour into the container 102 a liquid such as an agent or vehicle for the scent substance. Commonly this may be tap water, although other compounds such as alcohol or bleach are also possible.

Preferably, the user may fill the container 102 to approximately half full so that there remains a sizable chamber 102C space between the liquid level and the top of the container 102. Once the user has filled the container 102, the user can then add a portion of scent compound or any other compound into the agitator member 108. After which, the diffuser cover 106 can be replaced and the device 100 switched on.

Upon the device 100 being switched on and placed into operation, the motor 320 would drive the shaft 120 and in turn the agitator member 108 is rotated about the shaft 120. Once rotating, the agitator member 108 applies a centrifugal force to the liquid within the container 120 and drives the liquid upwards within the agitator member 108 to the top of the chamber 102C as shown by the flow arrow 301 of FIG. 3. Once the liquid is drawn to the top of the agitator member 108, it is then propelled in a circular manner towards to side wall of the container 102 to be cycled for the next entry into the agitator member 108. This continuous process thus allows for the continuous diffusion of the liquid into the air surrounding the device 100.

At least one of the abovementioned embodiments of the device for diffusing a compound may be advantageous in that the device provides for an effective and efficient method to diffuse a chemical substance, such as a scent compound, whilst providing an aesthetically pleasing appearance to a user. The combination of lighting effects and the movement of the liquid within the chamber also add to the aesthetic appeal of the device.

The term agitator member 108 includes members which are able to disturb the chemical compounds within the chamber 102C and may not necessarily be limited to stirrers or devices which form a stirring motion. In this sense, the term agitator member 108 may include pumping devices which cycle the chemical compounds from a first location to a second location within the chamber so as to disturb the chemical compound. In another embodiment of the device, the agitator member may not be limited to apply centrifugal force to draw the compound from the base portion of the chamber to the top portion of the chamber. Instead a pump mechanism connected to a nozzle may be used to draw and spray the compound within the container so that it can be diffused with the surrounding air and cycled within the container.

In another alternative embodiment, the agitator member 108 may have a plurality of fins which extend outwards from the outside surface of the agitator member 108. These fins will allow for a greater level of agitation by stirring the fluid within the chamber 102C and thus disturbing the chemical compounds further within the chamber for more diffusion.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. A device for diffusing a compound comprising:
   a chamber arranged to store a compound, the chamber including an agitator member arranged to disturb the compound within the chamber to diffuse the compound into air within the chamber; and
   a plurality of vents adapted to allow air to be drawn into the chamber and also to allow air to be expelled from the chamber when the agitator member is in an operating condition,
   wherein the agitator member has a narrow cylindrical end and a top end wider than the narrow end, the top end being positioned between the narrow end of the agitator and the plurality of vents, the agitator also having at least one conduit extending from the cylindrical end of the agitator member to the top end of the agitator member, the at least one conduit being arranged to provide liquid communication between a base portion and a top portion of the chamber, an inlet end of the conduit being coincident with a center of the narrow cylindrical end of the agitator member,
   wherein each of the plurality of vents is positioned closer to the top end of the agitator member than to the cylindrical end of the agitator member.

2. A device for diffusing a compound in accordance with claim 1, wherein the agitator member is arranged to disturb the compound such that air outside of the chamber is at least partially drawn into the chamber.

3. A device for diffusing a compound in accordance with claim 2, wherein the agitator member is further arranged to disturb the compound such that the air within the chamber is at least partially released from the chamber.

4. A device for diffusing a compound in accordance with claim 1, wherein when the agitator member disturbs the compound within the chamber, the compound is arranged to flow from the base portion of the chamber to the top portion of the chamber.

5. A device for diffusing a compound in accordance with claim 4, wherein the agitator member is arranged to rotate so as to apply centrifugal force onto the compound within the chamber.

6. A device for diffusing a compound in accordance with claim 5, wherein the centrifugal force is arranged to drive the compound from the base portion of the chamber to the top portion of the chamber.

7. A device for diffusing a compound in accordance with claim 6, wherein when upon the compound reaches the top portion of the chamber, the compound is propelled from the agitator member towards a sidewall of the chamber.

8. A device for diffusing a compound in accordance with claim 7, wherein the compound is diffused into the air within the chamber when the compound is propelled from the agitator member.

9. A device for diffusing a compound in accordance with claim 1, wherein the agitator member is of a truncated horn shape or frustum shape.

10. A device for diffusing a compound in accordance with claim 1, wherein the agitator member is rotated by a shaft connected to a motor.

11. A device for diffusing a compound in accordance with claim 1, wherein the motor is housed in a support base below the chamber.

12. A device for diffusing a compound in accordance with claim 1, wherein the compound includes a scented chemical substance.

* * * * *